(12) United States Patent
Sogaro (10) Patent No.: US 8,647,114 B2
(45) Date of Patent: Feb. 11, 2014

(54) APPARATUS FOR APPLYING A POWDERY OR LIQUID MATERIAL

(75) Inventor: Alberto C. Sogaro, Kronberg (DE)

(73) Assignee: Dispensys AG (CH)

( * ) Notice: Subject to any disclaimer, the term of this patent is extended or adjusted under 35 U.S.C. 154(b) by 0 days.

(21) Appl. No.: 12/743,630

(22) PCT Filed: Nov. 17, 2008

(86) PCT No.: PCT/DE2008/001898
§ 371 (c)(1),
(2), (4) Date: May 19, 2010

(87) PCT Pub. No.: WO2009/067986
PCT Pub. Date: Jun. 4, 2009

(65) Prior Publication Data
US 2010/0248179 A1    Sep. 30, 2010

(30) Foreign Application Priority Data

Nov. 26, 2007  (DE) .................. 10 2007 056 870
Apr. 3, 2008   (DE) .................. 20 2008 004 615 U (51) Int. Cl.
*A61C 3/02*   (2006.01)
(52) U.S. Cl.
USPC ............................................... 433/88
(58) Field of Classification Search
USPC ............. 222/165, 325, 399, 402.1, 402.14, 222/402.13, 635; 433/80, 88; 604/57, 58
See application file for complete search history.

(56) References Cited

U.S. PATENT DOCUMENTS

| | | | | | |
|---|---|---|---|---|---|
| 2,570,774 | A | * | 10/1951 | Davis ................... | 128/203.15 |
| 2,814,877 | A | * | 12/1957 | Tilden .................. | 433/88 |
| 3,157,323 | A | * | 11/1964 | Kitterman ............. | 222/520 |
| 3,277,922 | A | * | 10/1966 | Eisel .................... | 137/613 |
| 3,563,415 | A | * | 2/1971 | Ogle ..................... | 222/145.4 |
| 4,184,490 | A | * | 1/1980 | Jacklich ............... | 604/224 |
| 4,453,651 | A | * | 6/1984 | Braithwaite et al. ... | 222/82 |
| 4,657,534 | A | * | 4/1987 | Beck et al. ........... | 604/90 |
| 4,741,737 | A | * | 5/1988 | Meyer et al. ......... | 604/140 |
| 4,941,298 | A | * | 7/1990 | Fernwood et al. .... | 451/90 |
| 5,273,531 | A | * | 12/1993 | Knoepfler ............ | 604/58 |
| 5,501,596 | A | * | 3/1996 | Bailey .................. | 433/86 |

(Continued)

FOREIGN PATENT DOCUMENTS

| | | |
|---|---|---|
| DE | 90 14 519 U1 | 12/1990 |
| DE | 203 14 987 U1 | 1/2004 |

(Continued)

OTHER PUBLICATIONS

International Search Report under date of Mailing of Apr. 20, 2009 corresponding to PCT/DE2008/001898.

*Primary Examiner* — Cris L Rodriguez
*Assistant Examiner* — Matthew Saunders
(74) *Attorney, Agent, or Firm* — Quarles & Brady LLP (57) ABSTRACT

An apparatus for applying a powdery or liquid substance includes a delivery device having a delivery pressurant connector and a substantially tubular applicator. The tubular applicator has an upstream portion for connecting to the delivery pressurant connector (16) and a downstream delivery orifice for delivering the powdery or liquid substance. The applicator is provided with at least one reservoir for the powdery or liquid substance and at least one valve permitting, when opened, delivery of the powdery or liquid substance by means of the pressurant via the delivery orifice.

11 Claims, 7 Drawing Sheets

(56) References Cited

U.S. PATENT DOCUMENTS

| | | | |
|---|---|---|---|
| 5,772,084 A * | 6/1998 | Yale et al. | 222/402.1 |
| 5,941,702 A * | 8/1999 | Sharp et al. | 433/88 |
| 6,343,717 B1 * | 2/2002 | Zhang et al. | 222/209 |
| 6,416,321 B2 * | 7/2002 | Gugel et al. | 433/88 |
| 7,044,338 B2 * | 5/2006 | Roden | 222/153.11 |
| 7,131,784 B2 * | 11/2006 | Lee et al. | 401/128 |
| 7,198,485 B2 * | 4/2007 | Hamman | 433/88 |
| 2003/0180684 A1 * | 9/2003 | Sierro et al. | 433/88 |
| 2004/0094579 A1 * | 5/2004 | Tsutsui | 222/402.1 |
| 2005/0173465 A1 * | 8/2005 | Roden | 222/402.1 |
| 2007/0108235 A1 * | 5/2007 | Sogaro | 222/209 |
| 2007/0173771 A1 * | 7/2007 | Sogaro | 604/187 |

FOREIGN PATENT DOCUMENTS

| | | |
|---|---|---|
| EP | 1 346 700 A | 9/2003 |
| GB | 845 449 A | 8/1960 |
| JP | 2000 051234 A | 2/2000 |

\* cited by examiner

APPARATUS FOR APPLYING A POWDERY OR LIQUID MATERIAL

CROSS-REFERENCE TO RELATED APPLICATIONS

This application claims priority to PCT International Application No. PCT/DE08/001,898 filed on Nov. 17, 2008, which claims priority to German Application No. 10 2007 056 870.5 filed on Nov. 26, 2007, and German Application No. 20 2008 004 615.7 filed on Apr. 3, 2008, all of which are fully incorporated by referenced herein.

The invention relates to an apparatus for applying a powdery or liquid substance having the features as recited in the preamble of claim 1.

One such apparatus is known in practice, it constituting, for example, an aerosol can provided with a delivery tube as an applicator in the region of its spray head. The aerosol can itself is provided with a propellant or pressurant, a connector for the delivery tube being provided in the region of the spray head. The end of the delivery tube opposite the spray head features an orifice for delivering the powdery or liquid substance for application.

The invention is based on the object of providing an apparatus of the kind as aforementioned for use in meeting stringent hygiene demands in variable application.

This object is achieved in accordance with the invention by an apparatus having the features as set forth in claim 1.

The apparatus in accordance with the invention consequently comprises a delivery device including a delivery pressurant connector and a substantially tubular applicator with an upstream portion for connecting the delivery pressurant connector and a downstream delivery orifice for delivering the powdery or liquid substance, The applicator is provided with at least one reservoir for the powdery or liquid substance and at least one valve permitting, when opened, delivery of the powdery or liquid substance by means of the pressurant via the delivery orifice.

Consequently, in the apparatus in accordance with the invention the substance to be applied is reservoired directly in the applicator. The delivery device is used after opening of the valve to deliver the substance reservoired in the applicator to a surface being treated. More particularly, the applicator may be designed as a disposable device as used in medical or dental applications, now making it possible that stringent hygiene demands are safely satisfied in making use of the same pressurant source in the form of the delivery device.

The delivery device is, for instance, an aerosol can charged by compressed air or any other pressurant source available in any case, for example, in a dental practice.

The powdery or liquid substance reservoired in the applicator is, for example, a matting agent or antireflectant for application to a tooth stump to be imaged by means of a camera for production of a ceramic inlay or the like. However, it may just as well involve an aerosol local anaesthetic or the like.

The valve of the applicator in accordance with the invention makes sure that the powdery or liquid substance reservoired in the apparatus is not inadvertently delivered by the delivery orifice, for example, due to the delivery device being accidentally actuated.

In one special embodiment of the apparatus in accordance with the invention the valve comprises an inner shell closed off at one end, the end opposite thereto forming a portion of the applicator connectable to the delivery pressurant connector and its circumferential wall including at least one transverse opening, the inner shell being slidably guided at at least one sealing lip of an outer shell formed by a central tube so that the valve is either opened or closed depending on the position of the transverse opening in relation to the sealing lip.

It is also, of course, just as feasible that the portion of the applicator to be connected to the delivery pressurant connector is formed by an outer shell provided at its inner surface with an annular sealing lip for sliding guidance, the central tube in this case forming the inner shell, it comprising in this case at least one transverse opening whose opening in relation to the sealing lip configured at outer shell dictates the opening condition of the valve.

In one special embodiment of the apparatus in accordance with the invention the reservoir is arranged upstream from the valve and is formed by the inner shell. To render the powdery or liquid substance safely captive in the applicator, in this case, the corresponding shell, i.e. particularly the inner shell may be closed off at the end opposite the central tube by means of a foil which is pierced by the delivery pressurant connector when the applicator is mounted on the latter.

In an alternative embodiment of the apparatus in accordance with the invention the reservoir is arranged downstream of the valve, meaning that it is arranged in the region of the central tube. For example, the reservoir is formed by a receptacle formed radially in relation to the longitudinal centerline of the applicator. However, it is just as feasible too, that the reservoir is formed by a portion of enlarged diameter of the central tube of the applicator.

More particularly, when the substance reservoired in the applicator is a liquid and the reservoir is arranged in the region of the central tube then it is expedient that the central tube is separated by means of a second valve from an applicator tip comprising the delivery orifice so that the substance to be applied cannot be applied via the delivery orifice to a surface being treated until both valves have been opened.

Preferably the second valve comprises an inner shell closed off at one end, the end opposite thereto forming a portion of the applicator connectable to the delivery pressurant connector and its circumferential wall including at least one transverse opening, the inner shell being slidably guided at at least one sealing lip of an outer shell formed by a central tube so that the valve is either opened or closed depending on the position of the transverse opening in relation to the sealing lip. To activate the apparatus in accordance with the invention both valves then need to be opened, particularly by travelling both inner shells in the direction of the middle of the central tube so that the corresponding transverse opening negotiates the corresponding sealing lip permitting a thru-flow of the applicator with the pressurant and the substance to be applied from the upstream portion in conjunction with the delivery pressurant connector up to the delivery orifice. Displacing the inner shells in relation to the central tube is achievable in each case by axially shifting the corresponding inner shells and the central tube each relates to the other or by rotating each inner shell in relation to the central tube by means of a screwthread.

The term inner shell in the present context is to be appreciated in its broadest sense, it identifying, for example, a tubular piece closed off at one end and featuring circumferentially at least one port forming the transverse opening. This may also involve an arrangement in which each inner shell is a plunger-type plug engineered with an axial blind hole and a radially transverse passageway forming the at least one transverse opening porting into the axial blind hole.

The second valve too of the applicator may also be configured such that the inner shell is formed by the applicator tip and the outer shell by the central tube.

To create a connection between the applicator and the delivery pressurant connector of the delivery device capable of withstanding the pressure of the pressurant, the portion for connecting the delivery pressurant connector forms an inner taper mating with a corresponding outer taper of the delivery pressurant connector, the connection then substantially corresponding to the so-called Luer-type connection.

Furthermore, a means for locking the applicator to the delivery pressurant connector may be provided for a captive connector between the applicator and the delivery pressurant connector reservoiring a pressurant such as compressed air.

The apparatus in accordance with the invention may also be designed to house a multicomponent substance in which one of the components is reservoired in the central tube and at least one further component is reservoired in the inner shell(s). Mixing the components is done by telescoping the inner shell(s) and central tube in this application, whereby for the components the mixing chamber may also be provided preferably configured in the central tube. It is furthermore just as feasible to provide a plurality of inner shells nestingly telescoped, each holding a component of the multicomponent substance prior to being telescoped.

Further benefits and advantageous aspects of the subject matter of the invention are disclosed by the description, the drawing and the claims.

Illustrated diagrammatically simplified in the drawing are four example embodiments of the apparatus in accordance with the invention as detailed in the following description, whereby.

Figure 1:
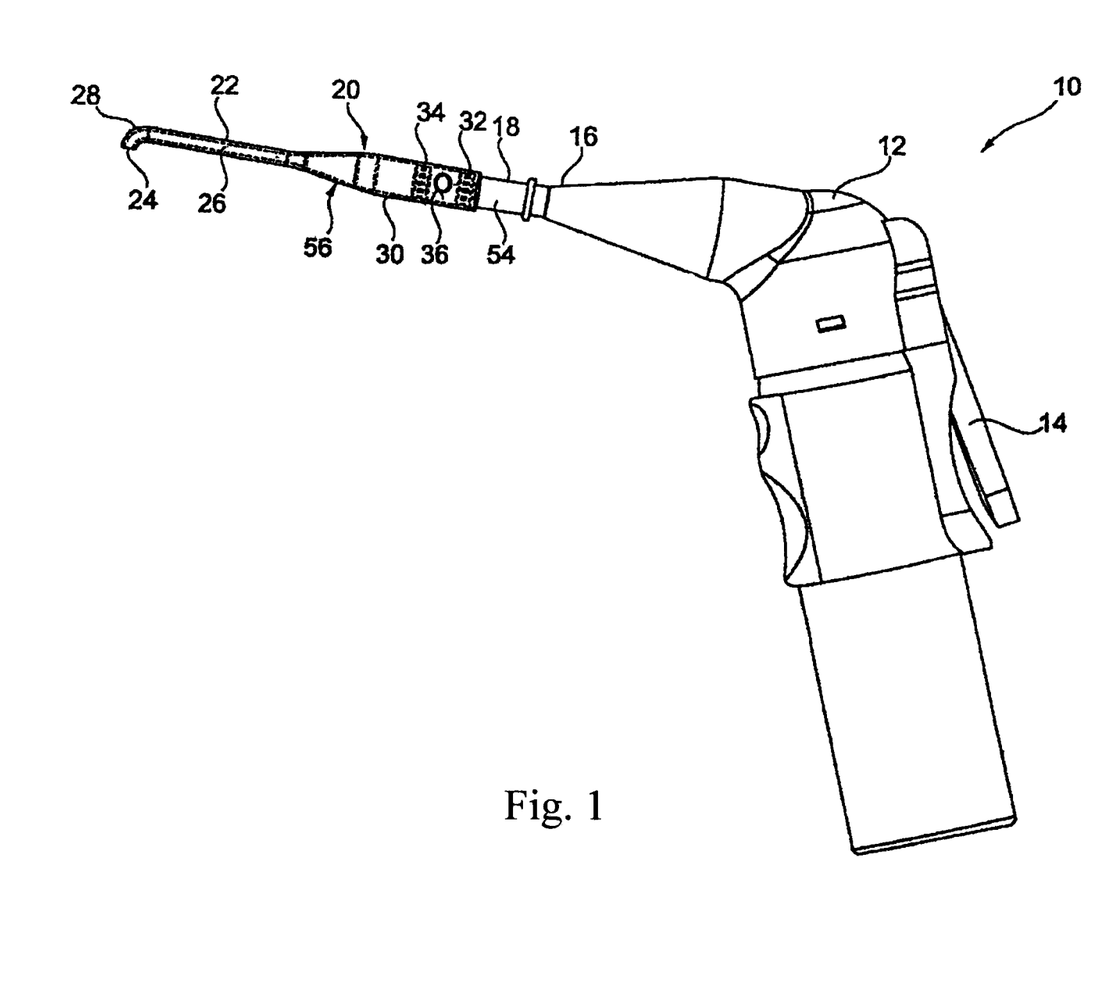
FIG. 1 depicts an apparatus for applying a matting agent to a tooth stump.

Referring now to FIG. 1 there is illustrated an apparatus 10 for applying a powdery matting agent or antireflectant to a tooth stump (not shown) to be imaged for production of a ceramic inlay.

The apparatus 10 comprises a delivery device 12 housing a pressurant, for example air, for delivery via a delivery nozzle 16 representing a delivery pressurant connector from the delivery device 12 by actuation of an actuating lever 14.

Mounted on the delivery nozzle 16 is an inner shell 18 of an applicator 20 provided with a central tube 56 as an applicator tip 22 configured at its end opposite the delivery device 12 with a delivery orifice 24. The central tube 56 forms an outer shell of the applicator 20. Slide-mounted in this central tube 56 is the inner shell 18 mounted on the delivery nozzle 16.

The applicator tip 22 comprises a straight portion 26 leading via a curved portion 28 to the delivery orifice 24 and which at the end opposite the delivery orifice 24 translates into a portion 30 having an enlargened diameter of the central tube 56 for slide-mounting the inner shell 18.

The portion 30 having an enlargened diameter of the central tube 56 comprises at its inner surface axially spaced away from each other, two annular sealing lips 32 and 34 for guiding the inner shell 18.

The inner shell 18 is configured tubular and is closed off at its end opposite the delivery device. In addition, the inner shell 18 comprises circumferentially, transverse openings 36 located between the sealing lips 32 and 34 when the applicator 20 is positioned deactivated. Contained in the interior of the inner shell 18 is the powder constituting the matting agent.

Application of the apparatus as shown in FIG. 1 is now detailed as follows:

Prior to application, i.e. prior to applying the matting agent, the delivery device 12 and an applicator 20 filled with powder are kept separate, whereby the open end of the inner shell 18 of the applicator 20 may be closed off by a foil or the like. When the matting agent is to be applied to a tooth/stump the applicator 20 is mounted on the delivery nozzle 16 of the delivery device 12 in thereby piercing the foil. After this, the inner shell 18 is slidingly positioned in relation to the central tube 56 so that the transverse openings 36 negotiate the sealing lip 34 to thus open up the flow path between the delivery nozzle 16, inner shell 18 and delivery orifice 24 of the applicator tip 22. Then, by actuating the actuating lever 14 a pressure surge can be exerted on the powder reservoired in the inner shell 18, delivering it via the transverse openings 36 into the applicator tip 22 and from there via the delivery orifice 24 to the tooth stump to be matted.

The applicator 20 including the inner shell 18 and central tube 56 represents a disposable tool, a new one of which is needed for the next patient.

The delivery device 12 must not necessarily be an aerosol can as shown. Alternatively, any pressurant source usual in any case in a dental practice may be connected to the applicator 20.

Furthermore the delivery device 12 with the actuating lever 14 may be provided with a swap can holding the necessary pressurant.

Figure 3:
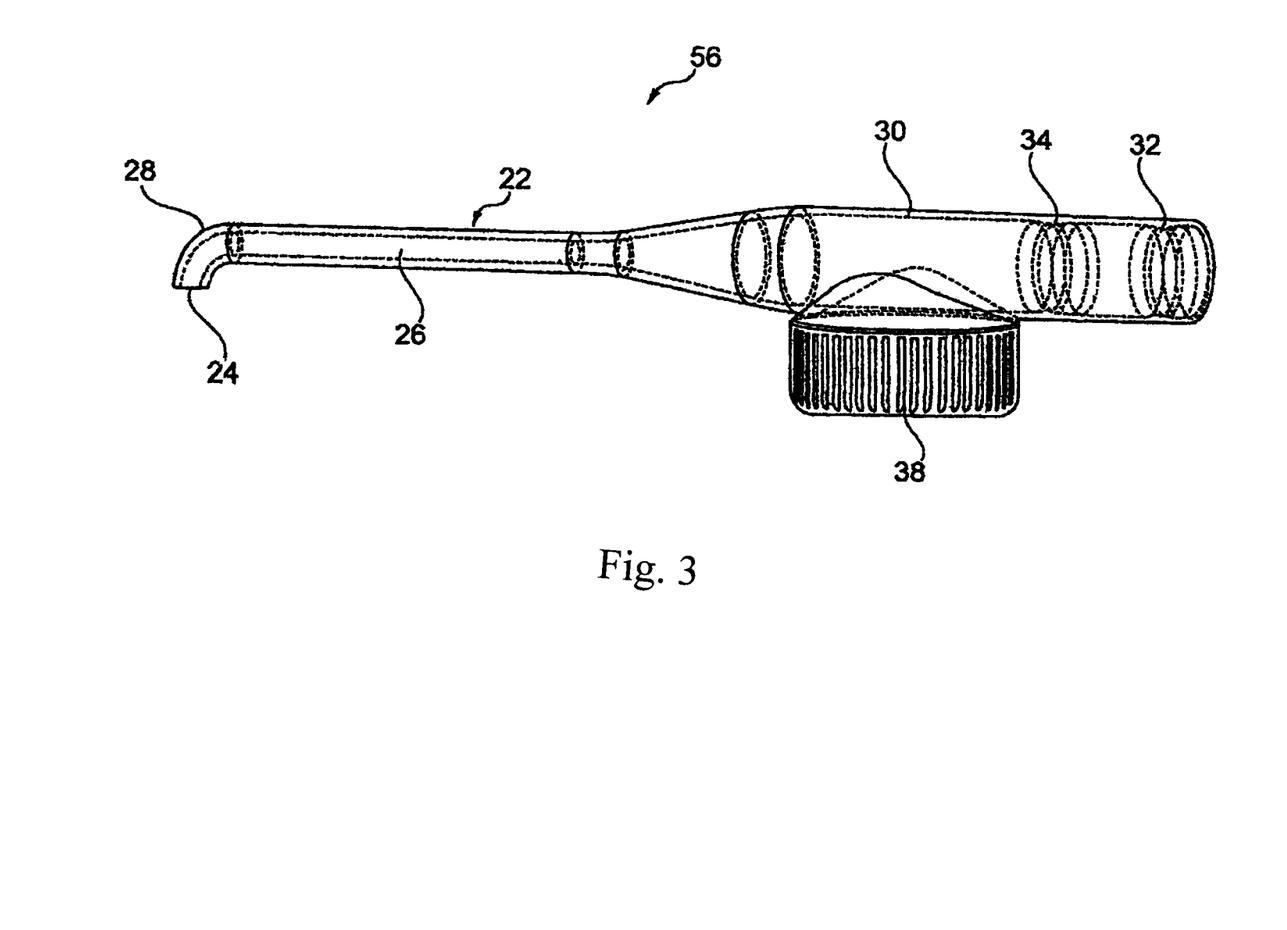
FIG. 3 depicts an alternative embodiment of an applicator tip.

Referring now to FIG. 3 there is illustrated an alternative embodiment of the apparatus configured in accordance with the invention in which the central tube 56 itself is provided with a powder reservoir 38 and which is consequently designed for repeated application. The powder reservoir 38 is engineered as a kind of cylindrical mount which in relation to the longitudinal centerline of the applicator 20 or of the central tube 56 is mounted radially on the portion 30 having the enlargened diameter. In this case no powder is reservoired in the inner shell 18 (not shown) corresponding to the inner shell of the embodiment as shown in FIG. 1. Also, there is no need in this case to close off the end opposite the delivery orifice 24 with a foil or the like. Instead, the powder is now safely reservoired in the powder reservoir once the inner shell inserted in the central tube 56 is in the deactivated position, i.e. when the transverse opening 36 is disposed between the two sealing lips 32 and 34.

To activate the apparatus the inner shell is urged into the central tube 56, the same as in the embodiment as shown in FIG. 1. The pressure surge created by the delivery device 12 aerosolizes the powder reservoired in the powder reservoir 38 and delivers it via the delivery orifice 24 as a function of the duration of the pressure surge.

Figure 2:
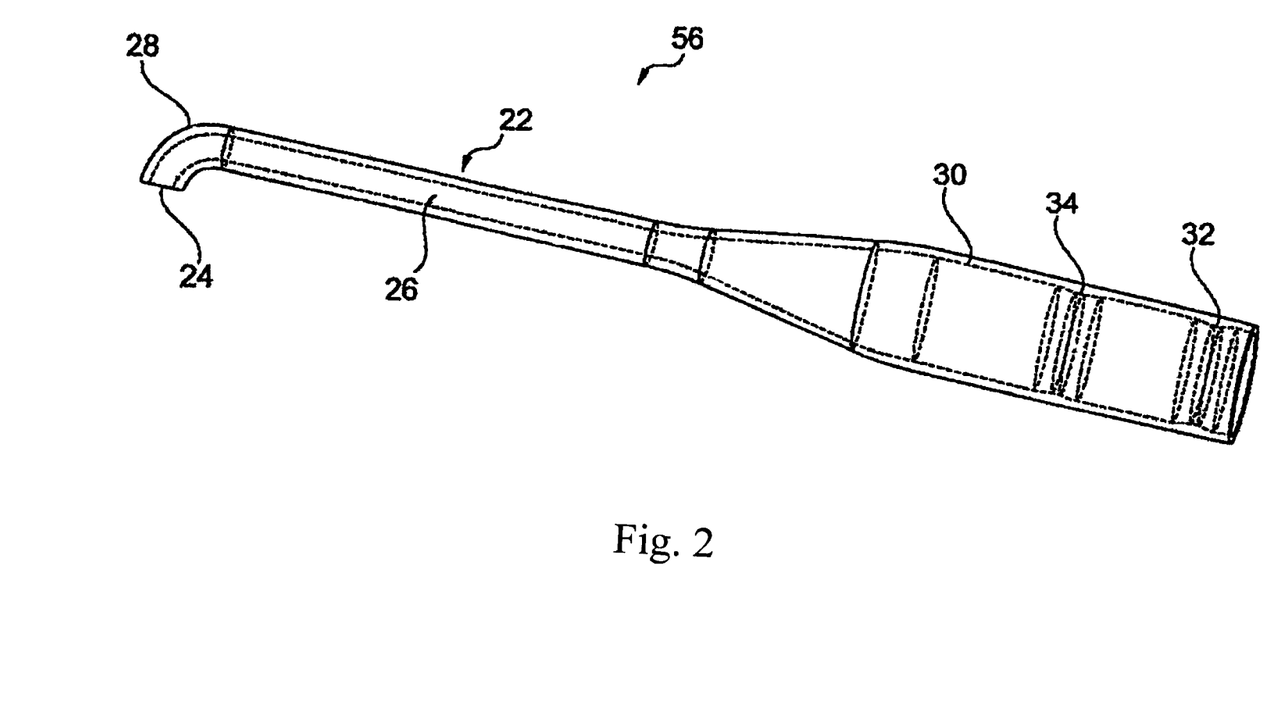
FIG. 2 depicts an applicator tip of the apparatus.
Figure 4:
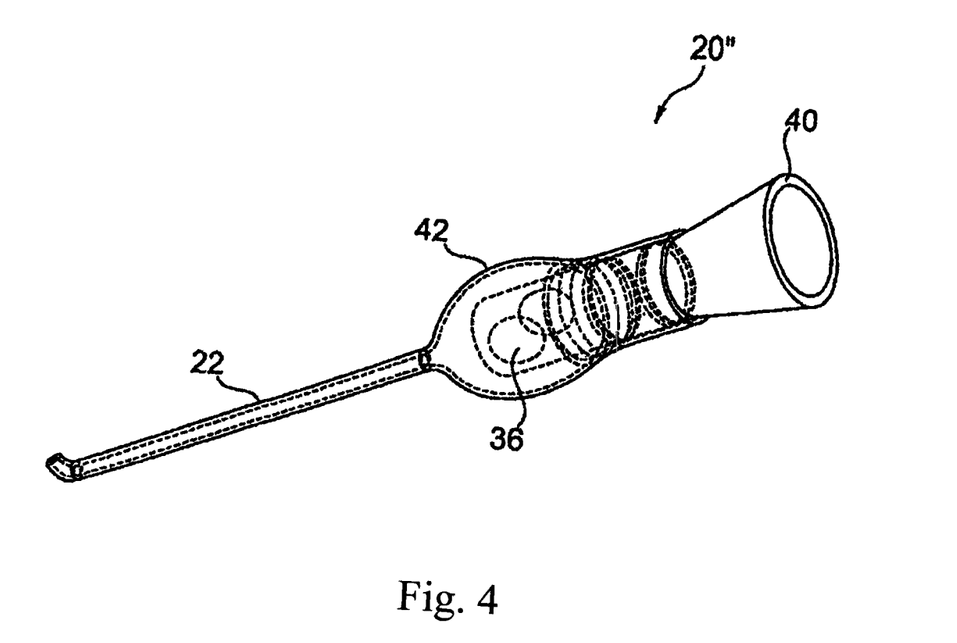
FIG. 4 depicts a third embodiment of an applicator tip together with a powder reservoir.
Figure 5:
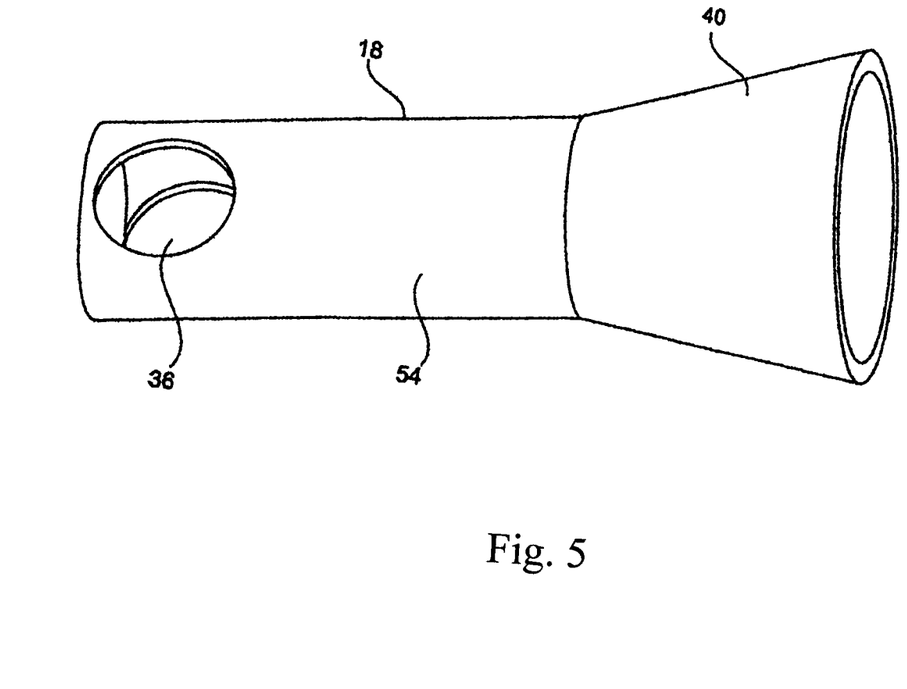
FIG. 5 depicts an inner shell of the applicator tip as shown in FIG. 4.
Figure 6:
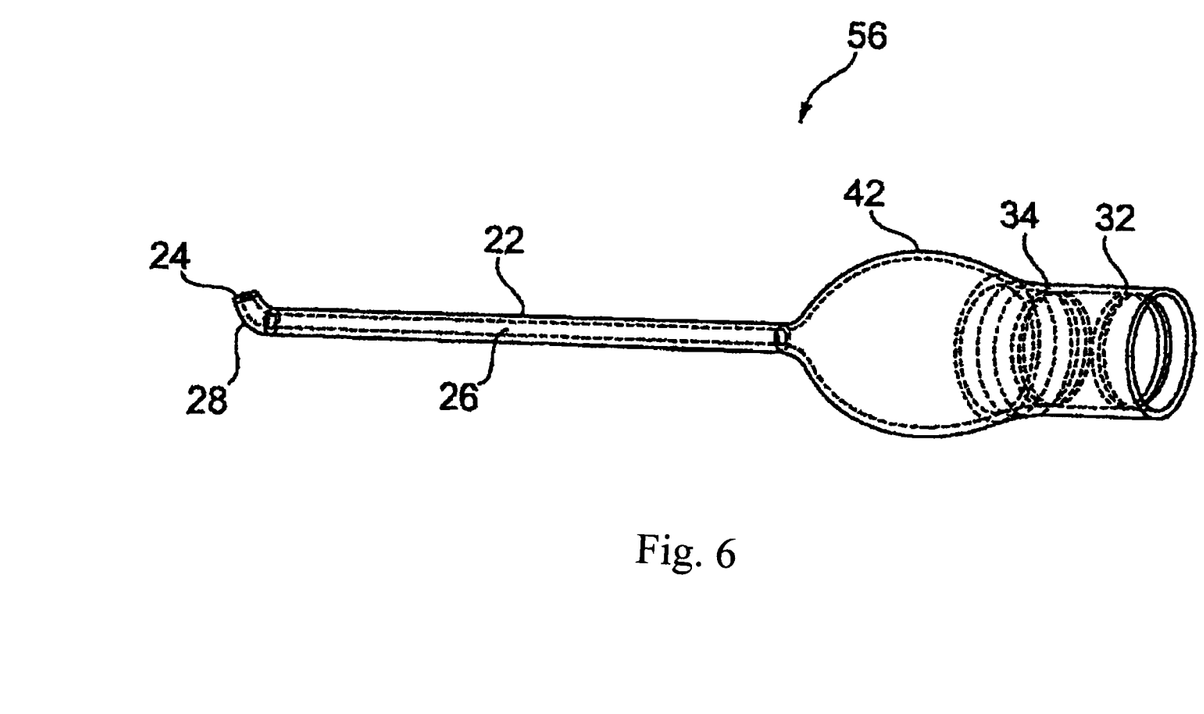
FIG. 6 depicts an outer shell of the applicator tip as shown in FIG. 5.

Referring now to FIGS. 4 to 6 there is illustrated a further embodiment of an apparatus designed in accordance with the invention essentially the same as that already shown in FIGS. 1 and 2 but differing by the inner shell 18 of applicator 20" comprising a funnelled, frusto-conical portion 40 for mounting as in a Luer system on an outer cone of a delivery device 12 not shown in this case. The downstream end of the funneled portion 40 serves as a stopper for the central tube 56 when the applicator is activated. In addition, when activated, the transverse openings 36 of the inner shell 18 are located in a bulged portion 42 of the central tube 56, resulting in a flow cross-section larger than in the embodiments as shown in FIGS. 1 and 2 between the inner shell 18 and the central tube 56 forming the outer shell.

Function and application of the applicator 20' as shown in FIGS. 4 to 6 correspond to the function and application of the applicator as shown in FIGS. 1 and 2.

Figure 7:
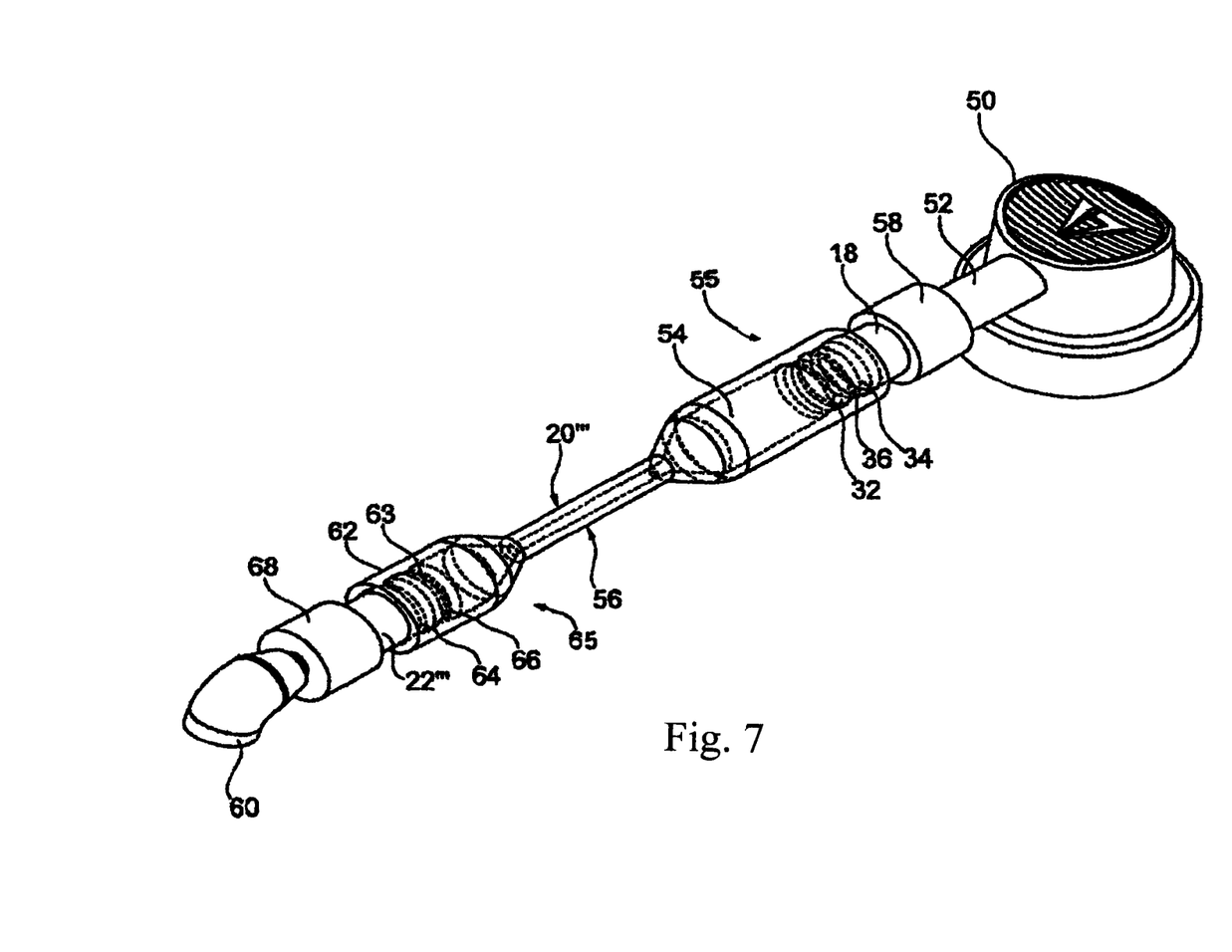
FIG. 7 depicts a further embodiment of an applicator of an apparatus in accordance with the invention.

Referring now to FIG. 7 there is illustrated a further embodiment of an applicator 20''' which is connected to a spray head 50 of an aerosol can (not shown) charged with compressed air. To connect the applicator 20''' the spray head 50 is provided with a delivery pressurant connector 52 configured as a substantially cylindrical nozzle. The applicator 20''' serves to apply a liquid, especially a liquid matting agent for application to a tooth stump (not shown) to be imaged by means of a camera for production of a ceramic inlay. In this arrangement, the matting agent is reservoired in a reservoir 54 of a central tube 56, more particularly in a portion having an enlargened diameter.

The central tube 56 is defined downstream by a first valve 55 formed by an inner shell 18 closed off at one end for mounting the delivery pressurant connector 52 of the spray head 50, its circumference featuring transverse openings 36 cooperating with the sealing lips 32 and 34 configured at the inner surface of the central tube 56. The inner shell 18 comprises furthermore an annular collar 58 serving as a stopper for the outer shell formed by the central tube 56.

At its downstream end the central tube 56 is connected via a second valve 65 to an applicator tip 22''' provided with an oral nozzle 60 forming the delivery orifice. The applicator tip 22''' forms, like the inner shell 18, an inner shell of the second valve slidingly guided in a second portion 62 of enlarged diameter of the central tube 56, the inner shell comprising at its inner surface two annular sealing lips 64 and 66 designed to cooperate with the transverse openings 63 of the applicator tip 22''' forming the inner shell.

The applicator tip 22''' too, comprises an annular collar 68 serving as a stopper for the portion 62 of enlarged diameter of the central tube 56.

To activate the applicator 20''' the two inner shells 18 and 22''' are urged until stopped in the central tube 56 to create a free flow path from the portion connecting the delivery nozzle 16, delivery pressurant connector 52 to the delivery orifice of the oral nozzle 60. Thus, actuating the delivery device delivers the liquid held in the reservoir 54 of the central tube 56 via the oral nozzle 60 in applying it to the surface for treatment.

The invention claimed is:

1. An apparatus for applying a powdery or liquid substance comprising a delivery device, said delivery device comprising:
   a delivery pressurant connector;
   a substantially tubular applicator with an upstream portion connecting the delivery pressurant connector and a downstream delivery orifice delivering the powdery or liquid substance, said applicator including a central tube and at least one reservoir for the powdery or liquid substance, said central tube including an outer shell having a radially inwardly extending annular sealing lip; and
   at least one valve including an inner shell closed off at one end and slidably received in the outer shell, at least one transverse opening formed through a circumferential wall of said inner shell, the inner shell being slidably guided by the annular sealing lip of the outer shell, so that the valve is either opened or closed depending on the position of the at least one transverse opening in relation to the sealing lip, such that when the valve is opened, the powdery or liquid substance is delivered via the delivery orifice by the pressurant delivered through the delivery pressurant connector and passing through the inner shell and out of the at least one transverse opening.

2. The apparatus as set forth in claim 1, in which the reservoir is arranged upstream from the valve and is formed by the inner shell.

3. The apparatus as set forth in claim 2, in which the inner shell of the valve is closed off at the end opposite the central tube by a foil which is pierced by the delivery pressurant connector when the applicator is mounted on the delivery pressurant connector.

4. The apparatus as set forth in claim 1, in which the reservoir is arranged downstream of the valve.

5. The apparatus as set forth in claim 4, in which the reservoir is mounted radially to the longitudinal centerline of the applicator.

6. The apparatus as set forth in claim 4, in which the reservoir is formed by a portion of enlarged diameter of the central tube of the applicator.

7. The apparatus as set forth in claim 4, in which the central tube is separated by a second valve from an applicator tip comprising the delivery orifice.

8. The apparatus as set forth in claim 7, in which the second valve comprises an inner shell closed off at one end, featuring at its circumferential wall at least one transverse opening and is guided by at least one sealing lip of an outer shell for opening and closing the second valve.

9. The apparatus as set forth in claim 8, in which the inner shell of the second valve is formed by the applicator tip and the outer shell is formed by the central tube.

10. The apparatus as set forth in claim 1, in which the portion for connecting the delivery pressurant connector forms an inner taper mating with a corresponding outer taper of the delivery pressurant connector of the delivery device.

11. The apparatus as set forth in claim 1, in which the applicator is locked to the delivery pressurant connector.

* * * * *

UNITED STATES PATENT AND TRADEMARK OFFICE
CERTIFICATE OF CORRECTION

PATENT NO.       : 8,647,114 B2
APPLICATION NO.  : 12/743630
DATED            : February 11, 2014
INVENTOR(S)      : Alberto C. Sogaro It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 112 days.

Signed and Sealed this

Twenty-ninth Day of September, 2015

Michelle K. Lee
*Director of the United States Patent and Trademark Office*